United States Patent [19]

Ellis et al.

[11] Patent Number: 4,769,239
[45] Date of Patent: Sep. 6, 1988

[54] VACCINE AGAINST VARICELLA-ZOSTER VIRUS

[75] Inventors: Ronald W. Ellis, Overbrook Hills; Paul M. Keller, Lansdale, both of Pa.

[73] Assignee: Merck & Co., Inc., Rahway, N.J.

[21] Appl. No.: 642,983

[22] Filed: Aug. 21, 1984

[51] Int. Cl.$^4$ .................... A61K 39/12; A61K 39/25; C12P 21/00; C12N 15/00

[52] U.S. Cl. ........................................ 424/89; 514/12; 435/68; 435/320; 536/27

[58] Field of Search .................... 435/235, 68; 424/89; 530/350; 514/12

[56] References Cited

PUBLICATIONS

Keller, P. et al., J. Virology, vol. 52, pp. 293–297, 1984.
Davison, A. et al., J. Virology, vol. 57, pp. 1195–1197, 1986.
Vafai, A. et al., J. Virology, vol. 52, pp. 953–959, 1984.
Asano, Y. et al., Biken Journal, vol. 23, pp. 95–106, 1980.
Okuno, T. et al., Virology, vol. 129, pp. 357–368, 1983.
Grose, C. et al., Injection and Immunity, vol. 40, pp. 381–388, 1983.
Chemical Abstracts, vol. 94, Abstract No. 43909m, 1981.
Chemical Abstracts, vol. 101, Abstract No. 189532t, 1984.
Chemical Abstracts, vol. 102, Abstract No. 20884a, 1985.
Chemical Abstracts, vol. 96, Abstract No. 156518t, 1982.
Chemical Abstracts, vol. 103, Abstract Nos. 155080v and 190709d, 1985.

*Primary Examiner*—Blondel Hazel
*Attorney, Agent, or Firm*—Donald J. Perrella; Hesna J. Pfeiffer

[57] ABSTRACT

A gene of varicella-zoster virus (VZV) which encodes immunogenic outer surface viral proteins has been identified through DNA sequence analysis. Fragments of the DNA have been cloned into a vector which, when placed into a host organism, expresses proteins which react with human convalescent zoster sera and with monoclonal antibodies which neutralize viral infectivity. These proteins are useful for preparation of a vaccine for VZV.

2 Claims, No Drawings

VACCINE AGAINST VARICELLA-ZOSTER VIRUS

BACKGROUND OF THE INVENTION

Chickenpox is caused by varicella-zoster virus (VZV), a member of the herpesvirus group. The disease occurs in persons with no prior VZV immunity. VZV-specific antibodies can be demonstrated shortly after onset of disease, decline during convalesence, but remain detectable for many years and correlate with immunity to the disease. Chickenpox is highly contagious; over 90% of the population becomes exposed to VZV during the first two decades. The disease is highly morbid to the immunosuppressed and to those beyond the second decade. In most, if not all cases, VZV becomes latent in dorsal root ganglion cells. From this latent state, VZV can reactivate and cause zoster even in the presence of specific antibodies, probably as a result of weakened cellular immunity.

VZV has six major glycoproteins on its surface: gp105, gp92, gp83, gp62, gp57, gp55. These glycoproteins apparently are the products of three genes: gA (gp105), gB (gp62, gp57) and gC (gp92, gp83, gp55). The gC glycoproteins are the majority and most immunogenic VZV glycoproteins. Some monoclonal antibodies to gA and gB display complement-independent neutralization, and monoclonal antibodies to gC display complement-dependent neutralization.

OBJECTS OF THE INVENTION

It is an object of the present invention to provide antigens which will prevent diseases associated with VZV infections. Another object is to provide antigens which can be used diagnostically to measure VZV antibody titers. Another object is to provide methods for the preparation of these antigens. Another object is to provide methods for using the antigens to raise antibodies, both in vivo and in vitro to VZV. Another object is to describe the full sequence of protein antigens which will include peptide antigens which may be synthesized by other means or expressed in other vectors. These and other objects of the present invention will be apparent from the following description.

SUMMARY OF THE INVENTION

The DNA sequence of the VZV gC gene has been identified. A fragment of the DNA has been cloned into a vector which, when placed in a host organism, expresses proteins which react with convalescent zoster sera and with neutralizing monoclonal antibodies to gC. These proteins are useful for preparation of a vaccine to VZV.

DETAILED DESCRIPTION OF THE INVENTION

The present invention is directed to identification of the VZV DNA which encodes the protective immunogenic glycoproteins gp92, gp83 and gp55. More specifically, it is directed to a 2.0 Kbp DNA fragment and to a 0.9 Kbp DNA fragment whose respective nucleotide sequences and amino acid sequences have been located within the known sequence of the entire VZV genome.

The present invention also is directed to vectors containing all or part of these 2.0 and 0.9 Kbp DNA fragments. The invention also is directed to host cells which contain these vectors and which cells are capable of expressing all or part of the peptides encoded by the 2.0 and 0.9 Kbp fragments. In accordance with known techniques, it will be obvious to those skilled in the art that parts of the foregoing peptides could be chemically synthesized or modified and retain their immunogenicity. Therefore, the present invention also is directed toward chemical synthesis of domains of these proteins, especially domains including and surrounding hydrophilic regions and threonine or serine and asparagine-X-serine or asparagine-X-threonine residues (wherein X is any amino acid), since these domains are likely to reside on the outer surface of the virus.

RNAs are isolated from cells producing VZV. These RNAs are preselected by hybridization to the HindIII-C, EcoRI-A, or EcoRI-E DNA fragments and translated in vitro. The polypeptide products are immunoprecipitated with monoclonal antibody specific for gC polypeptides. These DNA fragments select RNA which translates to the 70Kd precursor of the gp92, gp83 and gp55 gC neutralizing antigens.

The DNA segment which encodes RNA translatable to gC polypeptides is identified precisely as follows. VZV DNA is randomly digested and 0.3–1.5 Kbp fragments are inserted into the pORF2 expression vector. Bacteria transformed by the recombinant plasmids are screened with monoclonal antibodies for the production of gC antigens. Plasmid DNA from E. coli expressing gC antigens is hybridized to restriction fragments of VZV genomic DNA, and homology is identified within the HindIII-C fragment. DNA sequence analysis of the VZV DNA within the expression plasmid reveals identity to a 0.9 Kbp segment within the HindIII-C fragment whose DNA sequence is known. This 0.9 Kbp segment is part of a single long 2.0 Kbp open reading frame whose DNA sequence is known and which encodes a 70Kd immunogenic protein.

The hybrid protein containing VZV gC sequences derived from the 0.9 Kbp DNA segment is characterized with respect to serological reactivity. It is found to react with 8 of 11 convalescent zoster sera tested as well as with 7 of 8 neutralizing monoclonal antibodies to VZV gC. Therefore, this polypeptide segment carries neutralization epitopes as well as the majority of antigenicity associated with gC polypeptides.

Examples of suitable hosts for expression of VZV proteins include prokaryotic organisms, such as E. coli and B. subtilis, and eukaryotic organisms such as S. cerevisiae and continuous mammalian cell lines including Chinese Hamster ovary cells and diploid mammalian fibroblasts such as WI-38 and MRC-5 cells.

These proteins are usefully individually or in combination when placed in a physiologically acceptable carrier, e.g., saline or phosphate buffered saline, to protect against VZV disease when administered to a member of a susceptible mammalian species in amount of approximately 10 to 500 μg per dose, preferably from approximately 50 to 25 μg per dose. One or more doses may be administered to produce effective protection against VZV disease. The protein may be administered by injection, e.g., subcutaneously or intramuscularly. It is also to be understood that these proteins can be directly expressed in humans by means of appropriate viral expression vectors such as adeno, vaccinia, or herpes simplex.

The following examples illustrate the present invention without, however, limiting the same thereto. The disclosure of each reference mentioned in the following examples is hereby incorporated by reference.

EXAMPLE 1

DNA Fragments Which Select RNA Encoding the Precursor Protein to gC glycoproteins Cytoplasmic polyadenylated RNAs were prepared from VZV-infected MRC-5 cells as described (Biochemistry 18: 5294–5299, 1979). The RNAs encoded by the VZV DNA HindIII-C, EcoRI-A and EcoRI-E fragments were selected by hybridization to cloned VZV DNA (Proc. Natl. Acad. Sci. 79: 156–160, 1982) bound to nitrocellulose (J. Virology 37: 284–294, 1981). These RNAs were translated in a rabbit reticulocyte lysate are previously described (Evr. J. Biochem. 67: 247–254, 1976). The polypeptide products were immunoprecipitated with neutralizing monoclonal antibodies specific for VZV gC and with convalescent zoster serum. These DNA fragments select RNAs which include that which translates to the 70Kd gC precursor Okuno et al., Virology 129: 357–368, 1983).

EXAMPLE 2

Determination of the VZV DNA sequence which encodes gC antigens

A library of VZV DNA clones (Proc. Natl. Acad. Sci. 79: 156–160, 1982) was randomly digested by DNaseI in the presence of $Mn^{++}$ (Nucleic Acids Research 9: 3015–3027, 1981) in order to produce DNA in the size range of 0.1–2.5 Kbp. From this pool, DNA sized 0.3–1.5 Kbp was purified, made flush-ended, and cloned into the SmaI site of the pORF2 expression vector (Proc. Natl. Acad. Sci. 80: 4432–4436, 1983). The recombinant plasmids were introduced into E. coli TK1046 (λ1048). Bacterial colonies expressing hybrid proteins containing VZV polypeptides were selected, and such colonies were screened with monoclonal antibodies for the expression of VZV gC antigens. A colony expressing a VZV gC hybrid protein was isolated. The VZV antigens were recognized by 7 of 8 monoclonal antibodies to gC and by 8 of 11 convalescent zoster sera. The plasmid DNA from this colony was isolated and hybridized to restriction endonuclease digests of VZV genomic DNA (J. Mol. Biol. 98: 503–521, 1975). In this manner, the VZV insert in the bacterial plasmid was shown to be homologous to a 0.9 Kbp DNA sequence in the HindIII-C DNA clone. This segment of HindIII-C DNA, therefore, was identified as a part of the gC gene.

EXAMPLE 3

Determination of Nucleotide Sequences of the 0.9 and 2.0 Kbp segments of VZV DNA The complete nucleotide sequence of the VZV HindIII-C DNA segment contains several large open reading frames (EMBO Journal 2: 2203–2209, 1983). One of these open reading frames is 2.0 Kbp in length, encodes a 70Kd protein, and contains within it that 0.9 Kbp segment described in Example 2 which encodes VZV gC antigens.

A. The nucleotide sequence for the complete 2.0 Kbp segment which encodes the gC glycoprotein is given below:

| ATG | TTT | TAT | GAA | GCC | TTA | AAG | GCC | GAG | CTG | GTA | TAC | ACG |
|-----|-----|-----|-----|-----|-----|-----|-----|-----|-----|-----|-----|-----|
| AGA | GCA | GTC | CAT | GGT | TTT | AGA | CCT | CGG | GCG | AAT | TGC | GTG |
| GTT | TTA | AGT | GAC | TAT | ATT | CCG | AGG | GTC | GCC | TGT | AAT | ATG |
| GGG | ACA | GTT | AAT | AAA | CCT | GTG | GTG | GGG | GTA | TTG | ATG | GGG |
| TTC | GGA | ATT | ATC | ACG | GGA | ACG | TTG | CGT | ATA | ACG | AAT | CCG |
| GTC | AGA | GCA | TCC | GTC | TTG | CGA | TAC | GAT | GAT | TTT | CAC | ACC |
| GAT | GAA | GAC | AAA | CTG | GAT | ACA | AAC | TCC | GTA | TAT | GAG | CCT |
| TAC | TAC | CAT | TCA | GAT | CAT | GCG | GAG | TCT | TCA | TGG | GTA | AAT |
| CGG | GGA | GAG | TCT | TCG | CGA | AAA | GCG | TAC | GAT | CAT | AAC | TCA |
| CCT | TAT | ATA | TGG | CCA | CGT | AAT | GAT | TAT | GAT | GGA | TTT | TTA |
| GAG | AAC | GCA | CAC | GAA | CAC | CAT | GGG | GTG | TAT | AAT | CAG | GGC |
| CGT | GGT | ATC | GAT | AGC | GGG | GAA | CGG | TTA | ATG | CAA | CCC | ACA |
| CAA | ATG | TCT | GCA | CAG | GAG | GAT | CTT | GGG | GAC | GAT | ACG | GGC |
| ATC | CAC | GTT | ATC | CCT | ACG | TTA | AAC | GGC | GAT | GAC | AGA | CAT |
| AAA | ATT | GTA | AAT | GTG | GAC | CAA | CGT | CAA | TAC | GGT | GAC | GTG |
| TTT | AAA | GGA | GAT | CTT | AAT | CCA | AAA | CCC | AAA | GGC | CAA | AGA |
| CTC | ATT | GAG | GTG | TCA | GTG | GAA | GAA | AAT | CAC | CCG | TTT | ACT |
| TTA | CGC | GCA | CCG | ATT | CAG | CGG | ATT | TAT | GGA | GTC | CGG | TAC |
| ACC | GAG | ACT | TGG | AGC | TTT | TTG | CCG | TCA | TTA | ACC | TGT | ACG |
| GGA | GAC | GCA | GCG | CCC | GCC | ATC | CAG | CAT | ATA | TGT | TTA | AAA |
| CAT | ACA | ACA | TGC | TTT | CAA | GAC | GTG | GTG | GTG | GAT | GTG | GAT |
| TGC | GCG | GAA | AAT | ACT | AAA | GAG | GAT | CAG | TTG | GCC | GAA | ATC |
| AGT | TAC | CGT | TTT | CAA | GGT | AAG | AAG | GAA | GCG | GAC | CAA | CCG |
| TGG | ATT | GTT | GTA | AAC | ACG | AGC | ACA | CTG | TTT | GAT | GAA | CTC |
| GAA | TTA | GAC | CCC | GAG | ATT | GAA | CCG | GGT | GTC | TTG | AAA |
| GTA | CTT | CGG | ACA | GAA | AAA | CAA | TAC | TTG | GGT | GTG | TAC | ATT |
| TGG | AAC | ATG | CGC | GGC | TCC | GAT | GGT | ACG | TCT | ACC | TAC | GCC |
| ACG | TTT | TTG | GTC | ACC | TGG | AAA | GGG | GAT | GAA | AAA | ACA | AGA |
| AAC | CCT | ACG | CCC | GCA | GTA | ACT | CCT | CAA | CCA | AGA | GGG | GCT |
| GAG | TTT | CAT | ATG | TGG | AAT | TAC | CAC | TCG | CAT | GTA | TTT | TCA |
| GTT | GGT | GAT | ACG | TTT | AGC | TTG | GCA | ATG | CAT | CTT | CAG | TAT |
| AAG | ATA | CAT | GAA | GCG | CCA | TTT | GAT | TTG | CTG | TTA | GAG | TGG |
| TTG | TAT | GTC | CCC | ATC | GAT | CCT | ACA | TGT | CAA | CCA | ATG | CGG |
| TTA | TAT | TCT | ACG | TGT | TTG | TAT | CAT | CCC | AAC | GCA | CCC | CAA |
| TGC | CTC | TCT | CAT | ATG | AAT | TCC | GGT | TGT | ACA | TTT | ACC | TCG |
| CCA | CAT | TTA | GCC | CAG | CGT | GTT | GCA | AGC | ACA | GTG | TAT | CAA |
| AAT | TGT | GAA | CAT | GCA | GAT | AAC | TAC | ACC | GCA | TAT | TGT | CTG |
| GGA | ATA | TCT | CAT | ATG | GAG | CCT | AGC | TTT | GGT | CTA | ATC | TTA |
| CAC | GAC | GGG | GGC | ACC | ACG | TTA | AAG | TTT | GTA | GAT | ACA | CCC |
| GAG | AGT | TTG | TCG | GGA | TTA | TAC | GTT | TTT | GTG | GTG | TAT | TTT |
| AAC | GGG | CAT | GTT | GAA | GCC | GTA | GCA | TAC | ACT | GTT | GTA | TCC |
| ACA | GTA | GAT | CAT | TTT | GTA | AAC | GCA | ATT | GAA | GAG | CGT | GGA |
| TTT | CCG | CCA | ACG | GCC | GGT | CAG | CCA | CCG | GCG | ACT | ACT | AAA |

-continued

| | | | | | | | | | | | |
|---|---|---|---|---|---|---|---|---|---|---|---|
| CCC | AAG | GAA | ATT | ACC | CCC | GTA | AAC | CCC | GGA | ACG | TCA | CCA |
| CTT | CTA | CGA | TAT | GCC | GCA | TGG | ACC | GGA | GGG | CTT | GCA | GCA |
| GTA | GTA | CTT | TTA | TGT | CTC | GTA | ATA | TTT | TTA | ATC | TGT | ACG |
| GCT | AAA | CGA | ATG | AGG | GTT | AAA | GCC | TAT | AGG | GTA | GAC | AAG |
| TCC | CCG | TAT | AAC | CAA | AGC | ATG | TAT | TAC | GCT | GGC | CTT | CCA |
| GTG | GAC | GAT | TTC | GAG | GAC | TCG | GAA | TCT | ACG | GAT | ACG | GAA |
| GAA | GAG | TTT | GGT | AAC | GCG | ATT | GGA | GGG | AGT | CAC | GGG | GGT |
| TCG | AGT | TAC | ACG | GTG | TAT | ATA | GAT | AAG | ACC | CGG | TGA | |

The foregoing nucleotide sequence codes for the following amino acid sequence:

M F Y E A L K A E L
V Y T R A V H G F R
P R A N C V V A S D
Y I P K P V V G M G
T V N G I I T G V L
M G F G P V T G T L
R I T N P V R A T S
L R Y D D F H T D E
D K L D T N S V Y E
P Y Y H S D H A E S
S W V N R G E S S R
K A Y D H N S P Y I
W P R N D Y D G F L
E N A H E H H G V Y
N Q G R G I D G S E
R L M Q P T Q M S A
Q E D L G D D T G I
H V I P T L N G D D
R H K I V N V G D R
Q Y G D V F K G D L
N P K P Q G Q R L I
E V S V E E N H P F
T L R A P I Q R I Y
G V R Y T E T W S F
L P S L T C T G D A
A P A I Q H I C L K
H T T C F Q I D L V
D V D C A E N T K E
D Q L A E I S Y R F
Q G K K E A D Q P W
I V V N T S T L F D
E L E L D P P E I E
P G V L K V L R T E
K Q Y L G V Y I W N
M R G S D G T S G D
A T F L V T W K G A
E K T R N P T P F H
T P Q P Y G A E F V
M W D N Y H S H S H
V G Y T F S L A M F
L Q Y K I H E A Y P
D L L L E Q L P V L
I D P T C Y H M R A
Y S T C L S H P N G
P Q C L S P H L S Q
C T F T S V Y Q N C
R V A D T V T A Y F
E H A D N Y M D S T
L G I S L . H D G K T
G L I L H D G G T

-continued

L K F V D T P E S L
S G L Y V F V V Y F
N G H V E A V A Y T
V V S T V D H F V N
A I E E R G F P P T
A G Q P P A T T K P
K E I T P N P G T
S P L L R Y A A W T
G G L A A V V L L C
L V I F L I C T A K
R M R V K A Y R V D
K S P Y N Q S M Y D
A G L P V D D F E F
S E S T D T E E G T
G N A I G G S H G T
S R S Y T V Y I D K T

In the foregoing and succeeding sequences the letters represent the following amino acids:

| A | Ala | Alanine |
|---|---|---|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

B. The nucleotide sequence for 60 bases at each terminus of the 0.9 Kbp segment was determined and aligned with the published 6.2 Kbp DNA sequence. The 0.9 DNA sequence and the 35Kd gC protein segment, which encodes virtually all the major antigenicity of gC as well as neutralization epitopes, is given below:

| | | | | | | | | | | | |
|---|---|---|---|---|---|---|---|---|---|---|---|
| TTT | CAC | ACC | GAT | GAA | GAC | AAA | CTG | GAT | ACA | AAC | TCC | GTA |
| TAT | GAG | CCT | TAC | TAC | CAT | TCA | GAT | CAT | GCG | GAG | TCT | TCA |
| TGG | GTA | AAT | CGG | GGA | GAG | TCT | TCG | CGA | AAA | GCG | TAC | GAT |
| CAT | AAC | TCA | CCT | TAT | ATA | TGG | CCA | CGT | AAT | GAT | TAT | GAT |
| GGA | TTT | TTA | GAG | AAC | GCA | CAC | GAA | CAC | CAT | GGG | GTG | TAT |
| AAT | CAG | GGC | CGT | GGT | ATC | GAT | AGC | GGG | GAA | CGG | TTA | ATG |
| CAA | CCC | ACA | CAA | ATG | TCT | GCA | CAG | GAG | GAT | CTT | GGG | GAC |
| GAT | ACG | GGC | ATC | CAC | GTT | ATC | CCT | ACG | TTA | AAC | GGC | GAT |
| GAC | AGA | CAT | AAA | ATT | GTA | AAT | GTG | GAC | CAA | CGT | CAA | TAC |
| GGT | GAC | GTG | TTT | AAA | GGA | GAT | CTT | AAT | CCA | AAA | CCC | CAA |
| GGC | CAA | AGA | CTC | ATT | GAG | GTG | TCA | GTG | GAA | GAA | AAT | CAC |
| CCG | TTT | ACT | TTA | CGC | GCA | CCG | ATT | CAG | CGG | ATT | TAT | GGA |
| GTC | CGG | TAC | ACC | GAG | ACT | TGG | AGC | TTT | TTG | CCG | TCA | TTA |
| ACC | TGT | ACG | GGA | GAC | GCA | GCG | CCC | GCC | ATC | CAG | CAT | ATA |
| TGT | TTA | AAA | CAT | ACA | ACA | TGC | TTT | CAA | GAC | GTG | GTG | GTG |

-continued

| GAT | GTG | GAT | TGC | GCG | GAA | AAT | ACT | AAA | GAG | GAT | CAG | TTG |
| GCC | GAA | ATC | AGT | TAC | CGT | TTT | CAA | GGT | AAG | AAG | GAA | GCG |
| GAC | CAA | CCG | TGG | ATT | GTT | GTA | AAC | ACG | AGC | ACA | CTG | TTT |
| GAT | GAA | CTC | GAA | TTA | GAC | CCC | CCC | GAG | ATT | GAA | CCG | GGT |
| GTC | TTG | AAA | GTA | CTT | CGG | ACA | GAA | AAA | CAA | TAC | TTG | GGT |
| GTG | TAC | ATT | TGG | AAC | ATG | CGC | GGC | TCC | GAT | GGT | ACG | TCT |
| ACC | TAC | GCC | ACG | TTT | TTG | GTC | ACC | TGG | AAA | GGG | GAT | GAA |
| AAA | ACA | AGA | AAC | CCT | ACG | CCC | GCA | GTA | ACT | CCT | CAA | CCA |
| AGA |     |     |     |     |     |     |     |     |     |     |     |     |

The foregoing nucleotide sequence codes for the following amino acid sequence:

| F | H | T | D | E | D | K | L | D | T |
| N | S | V | Y | E | P | Y | Y | H | S |
| D | H | A | E | S | S | W | V | N | R |
| G | E | S | S | R | K | A | Y | D | H |
| N | S | P | Y | I | W | P | R | N | D |
| Y | D | G | F | L | E | N | A | H | E |
| H | H | G | V | Y | N | Q | G | R | G |
| I | D | S | G | E | R | L | M | Q | P |
| T | Q | M | S | A | Q | E | D | L | G |
| D | D | T | G | I | H | V | I | P | T |
| L | N | G | D | D | R | H | K | I | V |
| N | V | D | Q | R | Q | Y | G | D | V |
| F | K | G | D | L | N | P | K | P | Q |
| G | Q | R | L | I | E | V | S | V | E |
| E | N | H | P | F | T | L | R | A | P |
| I | Q | R | I | Y | G | V | R | Y | T |
| E | T | W | S | F | L | P | S | L | T |
| C | T | G | D | A | A | P | A | I | Q |
| H | I | C | L | K | H | T | T | C | F |
| Q | D | V | V | V | D | V | D | C | A |
| E | N | T | K | E | D | Q | L | A | E |
| I | S | Y | R | F | Q | G | K | K | E |
| A | D | Q | P | W | I | V | V | N | T |
| S | T | L | F | D | E | L | E | L | D |
| P | P | E | I | E | P | G | V | L | K |
| V | L | R | T | E | K | Q | Y | L | G |
| V | Y | I | W | N | M | R | G | S | D |
| G | T | S | T | Y | A | T | F | L | V |
| T | W | K | G | D | E | K | T | R | N |
| P | T | P | A | V | T | P | Q | P | R |

| D | L | N | P | K | P | Q | G | Q | R | L |
| I | E | V | S | V | E | E | N | H | P | F |
| T | L | R | A | P | I | Q | R | I | Y | G |
| V | R | Y | T | E | T | W | S | F | L | P |
| S | L | T | C | T | G | D | A | A | P | A |
| I | Q | H | I | C | L | K | H | T | T | C |
| F | Q | D | V | V | V | D | V | D | C | A |
| E | N | T | K | E | D | Q | L | A | E | I |
| S | Y | R | F | Q | G | K | K | E | A | D |
| Q | P | W | I | V | V | N | T | S | T | L |
| F | D | E | L | E | L | D | P | P | E | I |
| E | P | G | V | L | K | V | L | R | T | E |
| K | Q | Y | L | G | V | Y | I | W | N | M |
| R | G | S | D | G | T | S | T | Y | A | T |
| F | L | V | T | W | K | G | D | E | K | T |
| R | N | P | T | P | A | V | T | P | Q | P |
| R | G | A | E | F | H | M | W | N | Y | H |
| S | H | V | F | S | V | G | D | T | F | S |
| L | A | M | H | L | Q | Y | K | I | H | E |
| A | P | F | D | L | L | L | E | W | L | Y |
| V | P | I | D | P | T | C | Q | P | M | R |
| L | Y | S | T | C | L | Y | H | P | N | A |
| P | Q | C | L | S | H | M | N | S | G | C |
| T | F | T | S | P | H | L | A | Q | R | V |
| A | S | T | V | Y | Q | N | C | E | H | A |
| D | N | Y | T | A | Y | C | L | G | I | S |
| H | M | E | P | S | F | G | L | I | L | H |
| D | G | G | T | T | L | K | F | V | D | T |
| P | E | S | L | S | G | L | Y | V | F | V |
| V | Y | F | N | G | H | V | E | A | V | A |
| Y | T | V | V | S | T | V | D | H | F | V |
| N | A | I | E | E | R | G | F | P | P | T |
| A | G | Q | P | P | A | T | T | K | P | K |
| E | I | T | P | V | N | P | G | T | S | P |
| L | L | R | Y | A | A | W | T | G | G | L |
| A | A | V | V | L | L | C | L | V | I | F |
| L | I | C | T | A | K | R | M | R | V | K |
| A | Y | R | V | D | K | S | P | Y | N | Q |
| S | M | Y | Y | A | G | L | P | V | D | D |
| F | E | D | S | E | S | T | D | T | E | E |
| E | F | G | N | A | I | G | G | S | H | G |
| G | S | S | Y | T | V | Y | I | D | K | T |
| R. |   |   |   |   |   |   |   |   |   |   |

Either of the foregoing peptides may be formulated into a vaccine by admixing with a physiologically acceptable carrier and administering parenterally to susceptible mammalian species to induce formation of protective, including neutralizing, antibodies. The dosage level may be from about 5 to about 200 ug in from about one to about 3 doses.

What is claimed is:

1. A method of immunizing against VZV disease which comprises administering to a susceptible individual an immunologically effective amount of a polypetide having the amino acid sequence:

| M | F | Y | E | A | L | K | A | E | L | V |
| Y | T | R | A | V | H | G | F | R | P | R |
| A | N | C | V | V | L | S | D | Y | I | P |
| R | V | A | C | N | M | G | T | V | N | K |
| P | V | V | G | V | L | M | G | F | G | I |
| I | T | G | T | L | R | I | T | N | P | V |
| R | A | S | V | L | R | Y | D | D | F | H |
| T | D | E | D | K | L | D | T | N | S | V |
| Y | E | P | Y | Y | H | S | D | H | A | E |
| S | S | W | V | N | R | G | E | S | S | R |
| K | A | Y | D | H | N | S | P | Y | I | W |
| P | R | N | D | Y | D | G | F | L | E | N |
| A | H | E | H | H | G | V | Y | N | Q | G |
| R | G | I | D | S | G | E | R | L | M | Q |
| P | T | Q | M | S | A | Q | E | D | L | G |
| D | D | T | G | I | H | V | I | P | T | L |
| N | G | D | D | R | H | K | I | V | N | V |
| D | Q | R | Q | Y | G | D | V | F | K | G |

2. A method of immunizing against VZV disease which comprises administering to a susceptible individual an immunologically effective amount of a polypeptide having the amino acid sequence:

| F | H | T | D | E | D | K | L | D | T | N |
| S | V | Y | E | P | Y | Y | H | S | D | H |
| A | E | S | S | W | V | N | R | G | E | S |
| S | R | K | A | Y | D | H | N | S | P | Y |
| I | W | P | R | N | D | Y | D | G | F | L |
| E | N | A | H | E | H | H | G | V | Y | N |
| Q | G | R | G | I | D | S | G | E | R | L |
| M | Q | P | T | Q | M | S | A | Q | E | D |
| L | G | D | D | T | G | I | H | V | I | P |
| T | L | N | G | D | D | R | H | K | I | V |
| N | V | D | Q | R | Q | Y | G | D | V | F |
| K | R | L | I | E | V | S | V | E | E | N |
| P | F | T | L | R | A | P | I | Q | R | I |
| Y | G | V | R | Y | T | E | T | W | S | F |
| L | P | S | L | T | C | T | G | D | A | A |
| P | A | I | Q | H | I | C | L | K | H | T |

| | | | | | | | | | |
|---|---|---|---|---|---|---|---|---|---|
| T | C | F | Q | D | V | V | V | D | V | D |
| C | A | E | N | T | K | E | D | Q | L | A |
| E | I | S | Y | R | F | Q | G | K | K | E |
| A | D | Q | P | W | I | V | V | N | T | S |
| T | L | F | D | E | L | E | L | D | P | P |

| | | | | | | | | | |
|---|---|---|---|---|---|---|---|---|---|
| E | I | E | P | G | V | L | K | V | L | R |
| T | E | K | Q | Y | L | G | V | Y | I | W |
| N | M | R | G | S | D | G | T | S | T | Y |
| A | T | F | L | V | T | W | K | G | D | E |
| K | T | R | N | P | T | P | A | V | T | P |
| Q | P | R. | | | | | | | | |

* * * * *